US006417381B1

(12) United States Patent
Gedon et al.

(10) Patent No.: US 6,417,381 B1
(45) Date of Patent: Jul. 9, 2002

(54) PROCESS FOR PREPARING BIS(SILYLORGANO)AMINES

(75) Inventors: Steven C. Gedon, Williamstown; Melinda Hale, Belmont, both of WV (US); Michael P. Reynolds; Russell E. Malz, Jr., both of Naugatuck, CT (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/003,849

(22) Filed: Nov. 15, 2001

(51) Int. Cl.$^7$ ................................................. C07F 7/10
(52) U.S. Cl. ........................................................ 556/413
(58) Field of Search ......................................... 556/413

(56) References Cited

U.S. PATENT DOCUMENTS

| | | | |
|---|---|---|---|
| 2,930,809 A | * | 3/1960 | Jex et al. ..................... 556/413 |
| 3,046,295 A | | 7/1962 | Lisanke |
| 3,171,851 A | * | 3/1965 | Pepe ........................... 556/413 |
| 4,434,289 A | * | 2/1984 | Findeisen et al. ........ 556/413 X |
| 4,481,364 A | | 11/1984 | Chu et al. |
| 4,526,996 A | | 7/1985 | Kilgour et al. |
| 4,556,722 A | | 12/1985 | Quirk et al. |
| 4,927,949 A | | 5/1990 | Kabeta et al. |
| 5,001,246 A | | 3/1991 | Ishimura et al. |
| 5,075,506 A | | 12/1991 | Zimmermann |
| 5,097,073 A | | 3/1992 | Abe et al. |
| 5,101,055 A | | 3/1992 | Dinh et al. |
| 5,117,024 A | * | 5/1992 | Dinh et al. ................. 556/413 |
| 5,130,491 A | | 7/1992 | Zimmerman |
| 5,235,108 A | | 8/1993 | Borninkhof et al. |
| 5,247,109 A | | 9/1993 | Bank |
| 5,254,737 A | | 10/1993 | Zimmerman |
| 5,262,554 A | | 11/1993 | Bank |
| 5,283,348 A | | 2/1994 | Bank |
| 5,347,027 A | * | 9/1994 | Ritscher et al. ............. 556/413 |
| 5,536,860 A | | 7/1996 | Monkiewicz et al. |
| 5,567,847 A | | 10/1996 | Vedage et al. |
| 5,574,189 A | | 11/1996 | Vedage et al. |
| 5,808,123 A | | 9/1998 | Balduf et al. |
| 6,103,937 A | | 8/2000 | Baker et al. |
| 6,242,627 B1 | | 6/2001 | Gedon et al. |

FOREIGN PATENT DOCUMENTS

DE 4435390 11/1996

OTHER PUBLICATIONS

Freifelder, Morris; A Low Pressure Process for the Reduction of Nitriles. Use of Rhodium Catalyst, Practical Catalytic Hydrogenation: Techniques and Applications. (1971), 663 pp. Publisher: (Interscience, New York, N.Y.) CAN 75:10867 AN 1971:410867.

* cited by examiner

*Primary Examiner*—Paul F. Shaver
(74) *Attorney, Agent, or Firm*—Michael P. Dilworth

(57) ABSTRACT

A process is provided for preparing a bis(silylorgano)amine in which a cyanoorganosilane is reacted with hydrogen under hydrogenation conditions in the presence of a catalytically effective amount of hydrogenation catalyst selected from the group consisting of rhodium, ruthenium, palladium and platinum to produce the secondary aminoorganosilane.

14 Claims, No Drawings

PROCESS FOR PREPARING BIS(SILYLORGANO)AMINES

BACKGROUND OF THE INVENTION

This invention relates to a process for preparing bis(silylorgano)amines by the catalyzed reaction of a cyanoorganosilane with hydrogen.

Bis(silylorgano)amines such as the bis(trialkoxysilyl)alkylamines, bis(alkoxyalkylsilyl)alkylamines, and the like are a commercially important class of secondary aminoorganosilanes. They are useful, inter alia, as coupling agents for glass onto plastic and metal surfaces, as bonding aids, as additives to phenolic binder/foundry mixtures, as adhesion promoters for vinyl plastisols, polyurethane elastomers and epoxy and acrylic-based inks.

U.S. Pat. No. 5,101,055 discloses the production of mixtures of bis- and tris(silylorgano)amines by the coupling reaction of a primary aminoorganosilane in the presence of palladium monoxide catalyst. Similarly, U.S. Pat. No. 4,526,996 discloses a process for coupling silyl nitrites with primary amines in the presence of catalytically active quantities of palladium on carbon at 160° C. for 20 hours.

Several previously process patents also describe the hydrosilation of suitably substituted allyl amines as an alternative route to secondary amino silanes (U.S. Pat. No. 4,481,364 and DE 4,435,390).

U.S. Pat. No. 5,808,123 discloses the preparation of gamma-aminopropyltrialkoxysilanes as well as mixtures of primary and secondary aminosilanes by reacting gamma-chloropropyltrialkoxysilane with ammonia at elevated pressure and temperature. The reaction is preferably carried out at a temperature not exceeding 110° C. in order to suppress the formation of secondary amine, i.e., bis(trialkoxysilylpropyl)amine, and increase the selectivity of the reaction for the primary amine, i.e., gamma-aminopropyltrialkoxysilane.

U.S. Pat. No. 5,117,024 describes a process for preparing a primary aminoorganosilane by the reaction of a cyanoorganosilane with hydrogen in the presence of a supported cobalt catalyst. In the improvement of this process disclosed in U.S. Pat. No. 6,242,627, the reaction of cyanoorganosilane with hydrogen to provide primary aminorganosilane is carried out using a sponge cobalt catalyst, preferably in the presence of an alkali metal hydroxide to inhibit or suppress the formation of secondary aminoorganosilane.

SUMMARY OF THE INVENTION

In accordance with the present invention, a process for preparing a bis(silylorgano)amine is provided which comprises reacting a cyanoorganosilane with hydrogen under hydrogenation conditions in the presence of a catalytically effective amount of hydrogenation catalyst selected from the group consisting of rhodium, ruthenium, palladium, and/or platinum.

Unlike the process of U.S. Pat. No. 5,101,055 which, in addition to bis(silylorgano)amine, produces large amounts of tris(silylorgano)amine, and the process of U.S. Pat. No. 5,808,123 which prefers to minimize the production of bis(silylorgano)amine and increase the yield of the primary amine, the process of the present invention provides high selectivity for the bis(silylorgano)amine coproducing at most a minor amount of primary aminoorganosilane, e.g., not exceeding about 35 weight percent of the total product amines, and even lesser amounts of tris(silylorgano)amine, e.g., not exceeding about 10 weight percent of the total product amines. And, in contrast to the processes of U.S. Pat. Nos. 5,117,024 and 6,242,627 both of which emphasize the production of primary aminoorganosilane, the major product produced by the process of the present invention is bis(silylorgano)amine.

DESCRIPTION OF THE PREFERRED EMBODIMENTS

The starting cyanoorganosilane reactant referred to herein is preferably one possessing the general formula

in which case the product bis(silylorgano)amine will conform to the general formula

wherein each $R^1$ group is independently selected from the group consisting of alkyl, aryl and alkoxy groups of up to about 10 carbon atoms with at least one $R^1$ group being an aforesaid alkoxy group and each $R^2$ is the same or different divalent hydrocarbon group containing no ethylenic unsaturation and having up to about 20 carbon atoms.

The $R^1$ groups can be selected to be one or more of, for example, methyl, ethyl, propyl, isopropyl, butyl, tert-butyl, isobutyl, pentyl, dodecyl, methoxy, ethoxy, propoxy, isopropoxy, butoxy, phenyl or phenoxy. The $R^1$ groups are preferably selected from the group consisting of methyl, methoxy, ethyl and ethoxy. Whatever the nature of the $R^1$ groups, at least one of these groups must be an alkoxy group, e.g., any of the aforecited alkoxy groups.

Each divalent $R^2$ group can be, for example, a divalent group of an alkane, cycloalkane, aromatic or aralkane compound. Thus, the divalent $R^2$ groups can be, for example, the same or different linear or branched alkylene group such as methylene, ethylene, 1,2-propylene, 1,3-propylene, 2-methyl-1,3-propylene, 3-methyl-1,3-propylene, 3,3-dimethyl-1,3-propylene, ethylidene or isopropylidene, a cycloalkylene group such as cyclohexylene or cycloheptylene, an arylene group such as phenylene, tolylene, xylylene or naphthylene, or the divalent group $—C_6H_4—R^3—$ in which $R^3$ is methylene, ethylene, propylene, etc.

Examples of cyanoorganosilanes which can be hydrogenated by the process of this invention include 2-cyanoethyldimethylmethoxysilane, 2-cyanoethylmethyldimethoxysilane, 2-cyanoethyltrimethoxysilane, 2-cyanoethyltriethoxysilane, 2-cyanoethyldimethyl-ethoxysilane, 2-cyanoethylphenyldimethoxysilane, 2-cyanoethylphenyldiethoxysilane, 3-cyanomethyltriethoxysilane, 3-cyanopropyltrimethoxysilane, 3-cyanopropylmethyldimethoxysilane and 3-cyanopropylmethyldiethoxysilane.

It is preferred that the process herein be carried out in the presence of a molar excess of hydrogen, preferably two or more moles of hydrogen per mole of the selected cyanoorganosilane starting reactant. In general, the greater the amount of hydrogen present, the faster the reaction. Therefore, in a preferred mode of operating the process, hydrogen is added in excess at a concentration sufficient to maintain the pressure within the reactor within the range of from about 200 psig to about 2000 psig, and more preferably within the range from about 500 psig to about 1000 psig, since these pressures permit the use of standard high pressure reactors.

The present process can conventionally be conducted at a temperature within the range of from about 50° C. to about 250° C., and preferably at from about 100° C. to about 200° C.

The catalyst herein is at least one hydrogenation catalyst containing a metal selected from the group consisting of rhodium, ruthenium, palladium, and or platinum preferably on a refractory support such as carbon, silica, alumina, aluminosilica, a carbonate such as barium carbonate, diatomaceous earth, and the like. The amount of catalyst employed in the process of this invention can vary widely provided, of course, that a catalytically effective amount of the catalyst is present. Useful amounts of catalyst can range from about 0.05 to about 20 weight percent, and preferably from about 0.5 to about 1 weight percent, based on the weight of the cyanoorganosilane reactant.

It is convenient to add the hydrogenation catalyst to the reactor as a slurry, e.g., in a quantity of the intended principal bis(silylorgano)amine product or in the starting cyanoorganosilane.

The reaction of the starting cyanoorganosilane with hydrogen in the presence of hydrogenation catalyst to provide the desired bis(silylorgano)amine in accordance with this invention can be carried out in known and conventional high pressure reactors. The reactor can be, for example, a fixed bed, stirred-bed or fluidized-bed type reactor. The process can be run as a batch process or as a continuous process. A stirred-bed reactor is preferred. The reaction rate tends to be rapid, and is generally determined by the amount of catalyst, the pressure of the reactor, reaction temperature and related factors as appreciated by those skilled in the art. In general, residence times of from about 0.2 hours to about 5.0 hours provide acceptable results. When the process is run as a batch process, it is generally preferred to use residence times of from about 0.5 to about 3.0 hours accompanied by the addition of hydrogen as it is consumed by the reaction.

The presence of liquid water and/or water vapor is to be substantially avoided as water tends to result in the polymerization of any nitrile and/or aminoorganosilane to a polysiloxane. It is therefore advantageous to purge the reactor, once sealed, with an inert gas such as nitrogen to substantially remove any water that may be present.

The process of this invention can, if desired, be conducted in the presence of an organic solvent as the use of an organic solvent may increase the rate and/or yield of the process without, however, significantly affecting its selectivity for the desired bis(silylorgano)amine. The organic solvent can be a polar or non-polar solvent with a polar solvent, for example, an alkanol such as methanol, ethanol, propanol or isopropanol, being preferred. When using an alkanol solvent, it is preferred that the alkanol correspond to any alkoxy group(s) $R^1$ that may be present in the starting cyanoorganosilane reactant in order to minimize or avoid transesterification. Thus, when the starting cyanoorganosilane contains one or more methoxy groups (e.g., as in the case of the reactants 2-cyanoethyldimethyl-methoxysilane, 2-cyanoethylmethyldimethoxysilane, 2-cyanoethyltrimethoxysilane, 2-cyanoethyldimethoxysilane, 2-cyanoethylphenylmethoxysilane, and 3-cyanopropylmethyl-dimethoxysilane), the alkanol solvent of choice would be methanol. When the process is conducted as a batch process, it is preferred that the solvent be present at from about 5 to about 50 weight percent, and preferably from about 10 to about 20 weight percent, of the total reaction mixture. When the process is conducted as a continuous process and a solvent is utilized, the starting cyanoorganosilane reactant can be diluted in the solvent with the cyanoorganosilane comprising from about 50 to about 95 weight percent, and preferably from about 80 to about 90 weight percent, of the liquid feed to the reactor.

The product bis(silylorgano)amine, together with any coproduced primary aminorganosilane and tris(silylorgano) amine, can be recovered by any known or conventional procedure for separating liquid-solid mixtures and mixtures of liquids, for example, filtration and/or distillation. Any recovered mixture of amine can, if desired, be resolved by known and conventional means to provide the individual amines at high levels of purity.

Bis(silylorgano) amines that can be produced by the present process include, for example, bis[2-(trimethylsilyl) ethyl]amine, bis[2-(dimethylmethoxysilyl) ethyl]amine, bis [2-(methyldimethoxysilyl)ethyl]amine, bis[2-(trimethoxysilyl) ethyl]amine, bis[2-(triethoxysilyl)ethyl] amine, bis[3-(trimethyoxysilyl)propyl]amine, bis[3-(methyldi-methyoxysilyl)propyl]amine, and the like.

Of the following examples, the Comparative Example is presented as a contrast to Examples 1–10 which are illustrative of the process of this invention for obtaining bis (silylorgano)amine. In Tables 1–11 of the examples, the following terms have the indicated meanings:

"Nitrile": 2-cyanoethyltrimethoxysilane (CAS No. 2526-62-7; Silquest Y-9802 Silane, OSi Specialties, Sistersville, W.Va.).

"Primary Amine": 3-aminopropyltrimethoxysilane (CAS No. 13822-56-6; Silquest A-1110 Silane, OSi Specialties, Sistersville, W.Va.).

"Secondary Amine": Bis-[3-(trimethoxylsilyl)propyl]amine, (CAS No. 82985-35-11; Silquest A-1170 Silane, OSi Specialties, Sistersville, W.Va.).

"Tertiary amine": tris(trimethoxysilylpropyl)amine (CAS No. 82984-64-3).

COMPARATIVE EXAMPLE

This example illustrates the hydrogenation of a cyanoorganosilane employing a hydrogenation catalyst, which is outside the scope of the present invention.

In a 2 liter autoclave provided with a stirrer, cooling coil and sampling tube were added 1009.7 grams of 2-cyanoethyltrimethoxysilane (CAS No. 2526-62-7; Silquest Y-9802, OSi Specialties, Sistersville, W.Va.) and 4 grams of 55 wt. % nickel on kieselguhr (G49-B, Sud-Chemie Inc., Louisville, Ky.). After purging the autoclave with nitrogen and then hydrogen, the reactor was pressurized to 200 psig and the contents heated to 170° C. while stirring at 1130 rpm. After approximately 60 minutes, the reaction mass was cooled to room temperature for venting and discharge. Results of the reaction are shown in the Table 1.

TABLE 1

| Time (min) | Nitrile (wt. %) | Normalized Weight Percent Primary Amine (wt. %) | Secondary Amine (wt. %) | Tertiary Amine (wt. %) |
|---|---|---|---|---|
| 30 | 3.5 | 70.19 | 22.28 | 0.55 |
| 60 | 1.7 | 70.88 | 23.17 | 0.61 |

EXAMPLE 1

In a 2 liter autoclave provided with a stirrer, cooling coil and sampling tube were added 1037.2 grams of 2-cyanoethyltrimethoxysilane and 10 grams of 5 wt. % platinum on carbon (Johnson-Matthey Corp., West Deptford, N.J.). After purging the autoclave with nitrogen and then hydrogen, the reactor was pressurized to 400 psig and the contents heated to 110° C. while stirring at 1082 rpm. At approximately 100° C., hydrogen consumption began. After 30 minutes the reactor was vented to atmospheric pressure and re-charged with hydrogen to 400 psig. Although the hydrogen uptake appeared to stop after about 30 minutes, the reaction mass was allowed to remain under these conditions for another 2 hours before cooling to room temperature for venting and discharge. Samples were taken periodically during the reaction and the progress of the reaction is shown in Table 2.

TABLE 2

| Time (min) | Nitrile (wt. %) | Normalized Weight Percent Primary Amine (wt. %) | Secondary Amine (wt. %) | Tertiary Amine (wt. %) |
|---|---|---|---|---|
| 30 | 59.9 | 0.324 | 10.88 | 23.2 |
| 60 | 48.8 | 0.17 | 12.05 | 29.1 |
| 120 | 39.7 | 0.269 | 11.7 | 35.26 |
| 180 | 35.6 | 0.234 | 11.8 | 37.7 |

EXAMPLE 2

In a liter autoclave provided with a stirrer, cooling coil and sampling tube were added 970.7 grams of 2-cyanoethyltrimethoxysilane and 10 grams of 5 wt. % rhodium on carbon (Escat 340, Engelhard Corporation, Seneca, S.C.). After purging the autoclave with nitrogen and then hydrogen, the reactor was pressurized to 400 psig and the contents heated to 110° C. while stirring at 1082 rpm. At approximately 100° C., hydrogen consumption began. Although the hydrogen uptake appeared to stop after about 30 minutes, the reaction mass was allowed to remain under these conditions for another 30 minutes before cooling to room temperature for venting and discharge. Samples were taken periodically during the reaction and the progress of the reaction is shown in Table 3.

TABLE 3

| Time (min) | Nitrile (wt. %) | Normalized Weight Percent Primary Amine (wt. %) | Secondary Amine (wt. %) | Tertiary Amine (wt. %) |
|---|---|---|---|---|
| 30 | 3.17 | 25.15 | 65.3 | 1.4 |
| 60 | 2.8 | 25.25 | 66.17 | 1.2 |

EXAMPLE 3

In a 2 liter autoclave provided with a stirrer, cooling coil and sampling tube were added 964.1 grams of 2-cyanoethyltrimethoxysilane and 9.9 grams of 5 wt. % rhodium on carbon (Escat 340, Engelhard Corporation, Seneca, S.C.). After purging the autoclave with nitrogen and then hydrogen, the reactor was pressurized to 400 psig and the contents heated to 170° C. while stirring at 1187 rpm. At approximately 100° C., hydrogen consumption began and the temperature was allowed to increase to 177° C. Although the hydrogen uptake appeared to stop after about 30 minutes, the reaction mass was allowed to remain under these conditions for another 60 minutes before cooling to room temperature for venting and discharge. Samples were taken periodically during the reaction and the progress of the reaction is shown in Table 4.

TABLE 4

| Time (min) | Nitrile (wt. %) | Normalized Weight Percent Primary Amine (wt. %) | Secondary Amine (wt. %) | Tertiary Amine (wt. %) |
|---|---|---|---|---|
| 30 | 3.15 | 25.34 | 65.9 | 1.27 |
| 90 | 2.78 | 25.18 | 66.39 | 1.28 |

EXAMPLE 4

In a 2 liter autoclave provided with a stirrer, cooling coil and sampling tube were added 943.6 grams of 2-cyanoethyltrimethoxysilane and 4 grams of 5 wt. % rhodium on carbon (Escat 340, Engelhard Corporation, Seneca, S.C. After purging the autoclave with nitrogen and then hydrogen, the reactor was pressurized to 400 psig with continuous venting, and the contents heated to 180° C. while stirring at 1074 rpm. After approximately 30 minutes, the reaction mass was cooled to room temperature for venting and discharge. Results of the reaction are shown in Table 5.

TABLE 5

| Time (min) | Nitrile (wt. %) | Normalized Weight Percent Primary Amine (wt. %) | Secondary Amine (wt. %) | Tertiary Amine (wt. %) |
|---|---|---|---|---|
| 30 | 3.9 | 28.9 | 60.98 | 1.8 |

EXAMPLE 5

In a 2 liter autoclave provided with a stirrer, cooling coil and sampling tube were added 589.7 grams of 2-cyanoethyltrimethoxysilane and 4 grams of 5 wt. % rhodium on carbon (Escat 340, Engelhard Corporation, Seneca, S.C.). After purging the autoclave with nitrogen and then hydrogen, the reactor was pressurized to 400 psig with continuous venting, and the contents heated to 180° C. while stirring at 1174 rpm. After approximately 30 minutes, the reaction mass was cooled to room temperature for venting and discharge. Results of the reaction are shown in Table 6.

TABLE 6

| Time (min) | Nitrile (wt. %) | Normalized Weight Percent Primary Amine (wt. %) | Secondary Amine (wt %) | Tertiary Amine (wt. %) |
|---|---|---|---|---|
| 30 | 3.0 | 26.45 | 64.15 | 2.0 |

EXAMPLE 6

Experimental runs were carried out in a manner analogous to that of Example 5. Table 7 summarizes the results obtained using 5% Rh/carbon under the indicated conditions of temperature, pressure, and catalyst concentration.

TABLE 7

| Temperature (° C.) | Catalyst (g) | Pressure (psig) | Time (min.) | Nitrile (wt %) | Primary Amine (wt %) | Secondary Amine (wt %) | Tertiary Amine (wt %) |
|---|---|---|---|---|---|---|---|
| 118 | 4.0 | 400 | 30 | 3.28 | 23.439 | 51.35 | 1.29 |
| 122 | 1.0 | 400 | 30 | 61.05 | 9.16 | 14.53 | 6.4 |
|  |  |  | 60 | 8.68 | 28.4 | 51.07 | 2.7 |
|  |  |  | 90 | 5.06 | 29.9 | 55.876 | 2.6 |

TABLE 7-continued

| Temperature (° C.) | Catalyst (g) | Pressure (psig) | Time (min.) | Nitrile (wt %) | Primary Amine (wt %) | Secondary Amine (wt %) | Tertiary Amine (wt %) |
|---|---|---|---|---|---|---|---|
| 150 | 4.0 | 100 | 60 | 55.2 | 12.456 | 13.7 | 5.7 |
|  |  |  | 120 | 4.7 | 38.16 | 44.4 | 5.1 |
|  |  |  | 200 | 7.2 | 33.1 | 44.86 | 3.8 |
| 120 | 4.0 | 600 | 30 | 3.93 | 25.199 | 66.084 | 1.7 |
|  |  |  | 60 | 3.1 | 25.66 | 66.7 | 1.77 |

EXAMPLE 7

In a 2 liter autoclave provided with a stirrer, cooling coil and sampling tube were added 1008 grams of 2-cyanoethyltrimethoxysilane and 1 gram of 5 wt. % rhodium on carbon (G106N/D, Degussa Corporation, Culvert City, Ky.). After purging the autoclave with nitrogen and then hydrogen, the reactor was pressurized to 300 psig and the contents heated to 160° C. while stirring at 1071 rpm. At approximately 100° C., hydrogen consumption began. After approximately 30 minutes, the reaction mass was cooled to room temperature for venting and discharge. Results of the reaction are shown in Table 8.

TABLE 8

| Time (min) | Nitrile (wt. %) | Normalized Weight Percent Primary Amine (wt. %) | Secondary Amine (wt. %) | Tertiary Amine (wt. %) |
|---|---|---|---|---|
| 30 | 2.6 | 30.2 | 59.1 | 3.7 |

EXAMPLE 8

In a 2 liter autoclave provided with a stirrer, cooling coil and sampling tube were added 1018 grams of 2-cyanoethyltrimethoxysilane and 1 gram of 5 wt. % rhodium on carbon catalyst which had been recycled from Example 7. After purging the autoclave with nitrogen and then hydrogen, the reaction was pressurized to 300 psig and the contents heated to 160° C. while stirring at 1110 rpm. At approximately 100° C., hydrogen consumption began. After approximately 60 minutes, the reaction mass was cooled to room temperature for venting and discharge. Results of the reaction are shown in Table 9.

TABLE 9

| Time (min) | Nitrile (wt. %) | Normalized Weight Percent Primary Amine (wt. %) | Secondary Amine (wt. %) | Tertiary Amine (wt. %) |
|---|---|---|---|---|
| 30 | 2.9 | 21.8 | 41.9 | 7.3 |
| 60 | 2.7 | 30.5 | 57.58 | 4.4 |

EXAMPLE 9

In a 2 liter autoclave provided with a stirrer, cooling coil and sampling tube were added 1077 grams of 2-cyanoethyltrimethoxysilane and 1 gram of 5 wt. % rhodium on carbon (G106N/D, Degussa Corporation, Culvert City, Ky.). After purging the autoclave with nitrogen and then hydrogen, the reactor was pressurized to 300 psig and the contents heated to 90° C. while stirring at 1077 rpm. After approximately 80 minutes, the reaction mass was cooled to room temperature for venting and discharge. Results of the reaction are shown in Table 10.

TABLE 10

| Time (min) | Nitrile (wt. %) | Normalized Weight Percent Primary Amine (wt. %) | Secondary Amine (wt. %) | Tertiary Amine (wt. %) |
|---|---|---|---|---|
| 79 | 3.123 | 23.367 | 67.7 | 1.3 |

EXAMPLE 10

In a 2 liter autoclave provided with a stirrer, cooling coil and sampling tube were added 531 grams of 2-cyanoethyltrimethoxysilane and 2 grams of 5 wt. % ruthenium on carbon (5% Ru/C, lot C5007 Johnson-Matthey Corporation, West Deptford, N.J.). After purging the autoclave with nitrogen and then hydrogen, the reactor was pressurized to 300 psig and the contents heated to 100° C. while stirring at 1013 rpm. Although the hydrogen uptake appeared to stop after about 30 minutes, the reaction mass was allowed to remain under these conditions for another 30 minutes before cooling to room temperature for venting and discharge. Results of the reaction are shown in Table 11.

TABLE 11

| Time (min) | Nitrile (wt. %) | Normalized Weight Percent Primary Amine (wt. %) | Secondary Amine (wt. %) | Tertiary Amine (wt. %) |
|---|---|---|---|---|
| 60 | 3.2 | 24.5 | 64.6 | 2.0 |

What is claimed is:

1. A process for preparing a bis(silylorgano)amine which comprises reacting a cyanoorganosilane with hydrogen under hydrogenation conditions in the presence of a catalytically effective amount of hydrogenation catalyst selected from the group consisting of rhodium, ruthenium, palladium and platinum.

2. The process of claim 1 wherein the cyanoorganosilane possesses the general formula $$R^1_3SiR^2CN$$

and the product bis(silylorgano)amine possesses the formula $$(R^1_3SiR^2CH_2)_2NH$$

wherein each $R^1$ group is independently selected from the group consisting of alkyl, aryl and alkoxy group of up to about 10 carbon atoms with at least one $R^1$ group being an aforesaid alkoxy group and each $R^2$ is a divalent hydrocarbon group containing no ethylenic unsaturation and having of up to about 20 carbon atoms.

3. The process of claim 2 wherein the $R^1$ groups are independently selected from the group consisting of methyl, ethyl, propyl, isopropyl, butyl, tert-butyl, isobutyl, pentyl, dodecyl, methoxy, ethoxy, propoxy, isopropoxy, butoxy, phenyl and phenoxy and the $R^2$ groups are selected from the group consisting of methylene, ethylene, 1,2-propylene, 1,3-propylene, 2-methyl-1,3-propylene, 3-methyl-1,3-propylene, 3,3-dimethyl-1,3-propylene, ethylidene, isopropylidene, cyclohexylene, cycloheptylene, phenylene, tolylene, xylylene and naphthylene.

4. The process of claim 2 wherein the cyanoorganosilane is selected from the group consisting of 2-cyanoethyldimethylmethoxysilane, 2-cyanoethylmethyldimethoxysilane, 2-cyanoethyltrimethoxysilane, 2-cyanoethyltriethoxysilane, 2-cyanoethyldimethylethoxysilane, 2-cyanoethylphenyldimethoxysilane, 2-cyanoethylphenyldiethoxysilane, 3-cyanomethyltriethoxysilane, 3-cyanopropyltrimethoxysilane, 3-cyanopropylmethyldimethoxysilane and 3-cyanopropylmethyldiethoxysilane.

5. The process of claim 1 wherein the reaction is carried out in the presence of a molar excess of hydrogen at a pressure of about 200 psig to about 2000 psig and at a temperature of from about 50° C. to about 250° C.

6. The process of claim 1 wherein from about 0.05 to about 20 weight percent hydrogenation catalyst based on the weight of the cyanoorganosilane is employed.

7. The process of claim 1 wherein from about 0.5 to about 1 weight percent hydrogenation catalyst based on the weight of the cyanoorganosilane is employed.

8. The process of claim 1 wherein the hydrogenation catalyst is added as a slurry in a slurry-forming quantity of the desired bis(silylorgano)amine product.

9. The process of claim 1 carried out in the presence of a solvent for the cyanoorganosilane.

10. The process of claim 9 wherein the solvent is a polar solvent.

11. The process of claim 2 carried out in the presence of a solvent for the cyanoorganosilane.

12. The process of claim 2 wherein the solvent for the cyanoorganosilane is an alkanol corresponding to alkoxy group $R^1$ of the cyanoorganosilane.

13. The process of claim 1 wherein the hydrogenation catalyst is on a support.

14. The process of claim 1 carried out in the substantial absence of water.

* * * * *